US012232895B2

(12) United States Patent
Limoli et al.

(10) Patent No.: US 12,232,895 B2
(45) Date of Patent: Feb. 25, 2025

(54) MOBILE CT IMAGING SYSTEM COMPRISING A MOBILE CT IMAGING MACHINE WITH AN ON-BOARD DIGITAL RADIOGRAPHY IMAGER AND/OR AN ON-BOARD ULTRASOUND IMAGER

(71) Applicant: NeuroLogica Corporation, a subsidiary of Samsung Electronics Co., Ltd., Danvers, MA (US)

(72) Inventors: Michael Limoli, Merrimac, MA (US); Richard DeSalvo, Danvers, MA (US); Alexander Drosos, Lowell, MA (US)

(73) Assignee: NeuroLogica Corporation, a subsidiary of Samsung Electronics Co., Ltd., Danvers, MA (US)

( * ) Notice: Subject to any disclaimer, the term of this patent is extended or adjusted under 35 U.S.C. 154(b) by 252 days.

(21) Appl. No.: 18/080,984

(22) Filed: Dec. 14, 2022

(65) Prior Publication Data
US 2023/0181126 A1 Jun. 15, 2023

Related U.S. Application Data

(60) Provisional application No. 63/289,416, filed on Dec. 14, 2021.

(51) Int. Cl.
*A61B 6/03* (2006.01)
*A61B 6/00* (2006.01)
(Continued)

(52) U.S. Cl.
CPC ............ *A61B 6/035* (2013.01); *A61B 6/4233* (2013.01); *A61B 6/4266* (2013.01);
(Continued)

(58) Field of Classification Search
CPC .. A61B 6/00; A61B 6/03; A61B 6/032; A61B 6/035; A61B 6/4233; A61B 6/4266;
(Continued)

(56) References Cited

U.S. PATENT DOCUMENTS 8,888,364 B2 11/2014 Bailey et al.
10,039,505 B2 8/2018 Bailey et al.
(Continued)

FOREIGN PATENT DOCUMENTS

WO WO 2017/180569 10/2017

*Primary Examiner* — Jurie Yun
(74) *Attorney, Agent, or Firm* — Pandiscio & Pandiscio

(57) ABSTRACT

An imaging system for imaging an object, the imaging system comprising: a housing having a center opening; a CT imaging unit mounted to the housing, the CT imaging unit comprising: a rotatable disc extending around the center opening; an X-ray emitter mounted to the rotatable disc and configured to emit an X-ray beam; and an X-ray detector mounted to the rotatable disc in alignment with the X-ray beam; and a digital radiography imager comprising a detector plate mounted to the rotatable disc, the detector plate being configured to assume (i) a retracted position in which the detector plate is not aligned with the X-ray beam, whereby to permit the X-ray beam to contact the X-ray detector, and (ii) an extended position in which the detector plate is aligned with the X-ray beam, whereby to permit the X-ray beam to contact the detector plate.

15 Claims, 14 Drawing Sheets

(51) Int. Cl.
*A61B 6/42* (2024.01)
*A61B 8/00* (2006.01)

(52) U.S. Cl.
CPC .......... *A61B 6/4405* (2013.01); *A61B 6/4417* (2013.01); *A61B 6/4435* (2013.01); *A61B 6/4452* (2013.01); *A61B 8/461* (2013.01); *A61B 6/482* (2013.01)

(58) Field of Classification Search
CPC ... A61B 6/4405; A61B 6/4417; A61B 6/4435; A61B 6/4452; A61B 6/5247; A61B 6/482; A61B 8/00; A61B 8/15; A61B 8/4416; A61B 8/461
See application file for complete search history.

(56) References Cited

U.S. PATENT DOCUMENTS

| | | |
|---|---|---|
| 10,617,375 B2 | 4/2020 | Bailey et al. |
| 10,687,770 B2 | 6/2020 | Sullivan et al. |
| 11,903,749 B2 * | 2/2024 | Zilberstien ............. A61B 6/025 |
| 2020/0205756 A1 | 7/2020 | Bailey et al. |
| 2020/0367842 A1 | 11/2020 | Limoli et al. |

\* cited by examiner

MOBILE CT IMAGING SYSTEM COMPRISING A MOBILE CT IMAGING MACHINE WITH AN ON-BOARD DIGITAL RADIOGRAPHY IMAGER AND/OR AN ON-BOARD ULTRASOUND IMAGER

REFERENCE TO PENDING PRIOR PATENT APPLICATION

This patent application claims benefit of prior U.S. Provisional Patent Application Ser. No. 63/289,416, filed Dec. 14, 2021 by NeuroLogica Corporation, a subsidiary of Samsung Electronics Co. Ltd. and Michael Limoli et al. for MOBILE CT IMAGING SYSTEM COMPRISING A MOBILE CT IMAGING MACHINE WITH AN ON-BOARD DIGITAL RADIOGRAPHY IMAGER AND/OR AN ON-BOARD ULTRASOUND IMAGER.

The above-identified patent application is hereby incorporated herein by reference.

FIELD OF THE INVENTION

This invention relates to imaging systems in general, and more particularly to mobile anatomical imaging systems.

BACKGROUND OF THE INVENTION

Computerized Tomography (CT) In many situations it can be desirable to image the interior of opaque objects. By way of example but not limitation, in the medical field, it can be desirable to image the interior of a patient's body so as to allow viewing of internal structures without physically penetrating the skin of the patient.

Computerized Tomography (CT) has emerged as a key imaging modality in the medical field. CT imaging machines generally operate by directing X-rays into the body from a variety of positions, detecting the X-rays passing through the body, and then processing the detected X-rays so as to build a three-dimensional (3D) data set of the patient's anatomy. This 3D data set can then be processed so as to create a 3D computer model of the patient's anatomy. The 3D data set and 3D computer model can then be visualized so as to provide images (e.g., slice images, 3D computer images, etc.) of the patient's anatomy.

By way of example but not limitation, and looking now at FIGS. 1 and 2, there is shown an exemplary CT imaging machine 5. CT imaging machine 5 generally comprises a torus 10 which is supported by a base 15. A center opening 20 is formed in torus 10. Center opening 20 receives the patient anatomy which is to be scanned.

Looking next at FIG. 3, torus 10 generally comprises a fixed gantry 22, a rotating disc 23, an X-ray tube assembly 25 and an X-ray detector assembly 30. More particularly, fixed gantry 22 is disposed concentrically about center opening 20. Rotating disc 23 is rotatably mounted to fixed gantry 22. X-ray tube assembly 25 and X-ray detector assembly 30 are mounted to rotating disc 23 in diametrically-opposing relation, such that an X-ray beam 40 (generated by X-ray tube assembly 25 and detected by X-ray detector assembly 30) is passed through the patient anatomy disposed in center opening 20. Inasmuch as X-ray tube assembly 25 and X-ray detector assembly 30 are mounted on rotating disc 23 so that they are rotated concentrically about center opening 20, X-ray beam 40 will be passed through the patient's anatomy along a full range of radial positions, so as to enable CT imaging machine 5 to create a "slice" image of the anatomy penetrated by the X-ray beam. Furthermore, by moving the patient and CT imaging machine 5 relative to one another during scanning, a series of slice images can be acquired, and thereafter appropriately processed, so as to create a 3D data set of the scanned anatomy. This 3D data set can then be processed so as to create a 3D computer model of the scanned anatomy. It is common to configure X-ray detector assembly 30 so that multiple slices of images (e.g., 8 slices, 16 slices, 32 slices, etc.) may be acquired with each rotation of rotating disc 23, whereby to speed up the acquisition of scan data.

In practice, it is now common to effect helical scanning of the patient's anatomy so as to generate a 3D data set of the scanned anatomy, which can then be processed so as to create a 3D computer model of the scanned anatomy. The 3D data set and 3D computer model can then be visualized so as to provide images (e.g., slice images, 3D computer images, etc.) of the patient's anatomy.

The various electronic hardware and software for controlling the operation of rotating disc 23, X-ray tube assembly 25 and X-ray detector assembly 30, as well as for processing the acquired scan data so as to generate the desired slice images, 3D data set and 3D computer model, may be of the sort well known in the art and may be located in torus 10 and/or base 15.

The images produced by CT imaging machine 5 may be viewed on a display screen 41 provided on CT imaging machine 5 or on a remote screen (not shown).

Fixed CT Imaging Machine with Motorized Bed

In many cases, CT imaging machine 5 is intended to be stationary, in which case base 15 of CT imaging machine 5 is set in a fixed position on the floor of a room and a special motorized bed is provided to move the patient relative to CT imaging machine 5 during scanning. More particularly, and looking now at FIG. 4, with a stationary CT imaging machine 5A, the patient is brought to the location of CT imaging machine 5A, the patient is placed on the special motorized bed 42, and then the motorized bed 42 is used to move the patient relative to CT imaging machine 5A (i.e., to advance the patient into center opening 20 of CT imaging machine 5A) so that some (or all) of the length of the patient may be scanned by CT imaging machine 5A. Note that motorized bed 42 typically comprises a pedestal 44 and a patient support 46, with pedestal 44 being fixed in place relative to the stationary CT imaging machine 5A and the patient support 46 moving relative to pedestal 44 (and relative to stationary CT imaging machine 5A). Note also that patient support 46 is typically formed out of a radiolucent material so as to not interfere with CT imaging of the patient.

Mobile CT Imaging Machine

In other cases, CT imaging machine 5 is intended to be mobile so that the CT imaging machine may be brought to the patient and the patient scanned at the patient's current location, with the CT imaging machine moving relative to the patient during scanning. Scanning the patient with a mobile CT imaging machine 5 can be highly advantageous, since it can reduce delays in patient scanning (e.g., the patient can be scanned in an emergency room rather than waiting to be transported to the radiology department) and/or it can allow the patient to be scanned without requiring movement of the patient (e.g., the patient can be scanned at their bedside in an intensive care unit, "ICU").

To this end, and looking now at FIGS. 5 and 6, base 15 of a mobile CT imaging machine 5B may comprise a transport assembly 50 for (i) moving mobile CT imaging machine 5B to the location of the patient prior to scanning, and (ii) moving the CT imaging machine 5B relative to the patient during scanning. More particularly, transport assembly 50 preferably comprises (i) a gross movement mechanism 55 for moving CT imaging machine 5B relatively quickly across room distances, so that the CT imaging machine can be quickly and easily brought to the bedside of the patient, such that the patient can be scanned at their bedside without needing to be moved to a radiology department, and (ii) a fine movement mechanism 60 for moving the CT imaging machine precisely, relative to the patient, during scanning so that the patient can be scanned on their bed or gurney without needing to be moved onto a special motorized bed.

In one preferred form of the invention, gross movement mechanism 55 preferably comprises a plurality of free-rolling casters 62, and fine movement mechanism 60 preferably comprises a plurality of centipede belt drives 63 (which can be configured for either stepped or continuous motion, whereby to provide either stepped or continuous scanning of the patient). Hydraulic apparatus 65 permits either gross movement mechanism 55 or fine movement mechanism 60 to be engaged with the floor, whereby to facilitate appropriate movement of mobile CT imaging machine 5B.

Thus, with mobile CT imaging machine 5B, the mobile CT imaging machine may be pre-positioned in an "out of the way" location (e.g., in an unused corner of an emergency room) and then, when a patient requires scanning, the patient may be quickly and easily scanned at their bedside, i.e., by simply moving the mobile CT imaging machine to the patient's bedside on gross movement mechanism 55 (e.g., on casters 62), and thereafter moving the mobile CT imaging machine during scanning on fine movement mechanism 60 (e.g., on centipede belt drives 63).

Note that other mobile CT imaging machines are known in the art.

By way of example but not limitation, and looking now at FIG. 7, there is provided a mobile CT imaging machine 5C which is substantially the same as mobile CT imaging machine 5B, except that (i) gross movement mechanism 55 of mobile CT imaging machine 5B is replaced by gross movement mechanism 55C of mobile CT imaging system 5C, wherein gross movement mechanism 55C comprises a plurality of powered mecanum wheels 70 (also known as "omni" wheels or "ilon" wheels) for providing mobile CT imaging machine 5C with omnidirectional powered movement, and (ii) fine movement mechanism 60 of mobile CT imaging machine 5B is replaced by fine movement mechanism 60C of mobile CT imaging machine 5C, wherein fine movement mechanism 60C comprises a plurality of powered wheels 63C for moving mobile CT imaging machine 5C during scanning. See, for example, U.S. Pat. No. 10,687,770, issued Jun. 23, 1920 to NeuroLogica Corporation, a subsidiary of Samsung Electronics Co., Ltd., for MOBILE ANATOMICAL IMAGING SYSTEM WITH IMPROVED MOVEMENT SYSTEM, which patent is hereby incorporated herein by reference. By way of further example but not limitation, and looking now at FIG. 8, there is provided a mobile CT imaging machine 5D which is provided with so-called "Liddiard wheels" 76, wherein each Liddiard wheel 76 can be independently rotated (i) about the axis of rotation of powered axle 78, and/or (ii) about its toroidal axis (i.e., orthogonal to the axis of rotation of powered axle 78), whereby to permit mobile CT imaging machine 5D to be moved in any direction (e.g., over long distances when being brought to the patient and over short distances during scanning of the patient). By selectively driving each of the Liddiard wheels 76 in a coordinated fashion, omnidirectional powered movement of mobile CT imaging machine 5D can be achieved. Thus, Liddiard wheels 76 are essentially motorized wheels which, when operated in a coordinated fashion, can provide onmidirectional drive for mobile CT imaging machine 5D, with mobile CT imaging machine 5D being steered by adjusting (i) the direction and rate of rotation of the various powered axles 78, and/or (ii) the direction and rate of rotation of the various tires 79 around their toroidal axes. Significantly, Liddiard wheels 76 can provide omnidirectional drive for mobile CT imaging machine 5D without requiring pivoting (i.e., "steering") of Liddiard wheels 76 relative to mobile CT imaging machine 5D. See, for example, U.S. Pat. No. 11,369,326, issued Jun. 28, 1922 to NeuroLogica Corporation, a subsidiary of Samsung Electronics Co., Ltd., for MOBILE ANATOMICAL IMAGING SYSTEM WITH IMPROVED MOVEMENT SYSTEM COMPRISING LIDDIARD WHEELS, which patent is hereby incorporated herein by reference.

The Need for a Mobile CT Imaging Machine Comprising an On-Board Digital Radiography Imager In addition to the foregoing, in some circumstances a patient being scanned with a mobile CT imaging machine may also have a condition which is susceptible to being separately scanned with a digital radiography imager. In this case, it may be desirable to scan the patient with a digital radiography imager, rather than with CT, in order to reduce the radiation exposure of the patient. As used herein, the term "digital radiography imager" is intended to refer to substantially any form of X-ray imaging that relies on an X-ray sensitive detector (e.g., an X-ray sensitive plate) configured to convert the X-ray radiation incident on the X-ray sensitive detector into an equivalent electric charge which can then be utilized in order to generate an image, as will be apparent to one of skill in the art. It would, therefore, be desirable to provide a mobile CT imaging machine comprising an on-board digital radiography imager so that the mobile CT imaging machine and the on-board digital radiography imager can be moved as a single unit to the patient, whereby to permit scanning of the patient using the desired imaging modality (e.g., CT and/or digital radiography).

Thus there exists a need for a new and improved mobile CT imaging machine comprising an on-board digital radiography imager.

The Need for a Mobile CT Imaging Machine Comprising an On-Board Ultrasound Imager In addition to the foregoing, in some circumstances a patient being scanned with a mobile CT imaging machine may also have a condition which is susceptible to being separately scanned with an ultrasound imager. In this case, it may be desirable to scan the patient with an ultrasound imager, rather than with CT (or with a digital radiography imager), in order to reduce (or eliminate) the radiation exposure of the patient. It would, therefore, be desirable to provide a mobile CT imaging machine comprising an on-board ultrasound imager so that the mobile CT imaging machine and the on-board ultrasound imager can be moved as a single unit to the patient, whereby to permit scanning of the patient using the desired imaging modality (e.g., CT and/or ultrasound).

Thus there also exists a need for a new and improved mobile CT imaging machine comprising an on-board ultrasound imager.

SUMMARY OF THE INVENTION

These and other objects of the present invention are addressed by the provision and use of a new and improved mobile CT imaging system which comprises a mobile CT imaging machine with an on-board digital radiography imager and/or an on-board ultrasound imager.

In one preferred form of the invention, there is provided an imaging system for imaging an object, the imaging system comprising:
 a housing having a center opening;
 a CT imaging unit mounted to the housing, the CT imaging unit comprising:
  a rotatable disc extending around the center opening;
  an X-ray emitter mounted to the rotatable disc and configured to emit an X-ray beam; and
  an X-ray detector mounted to the rotatable disc in alignment with the X-ray beam; and
 a digital radiography imager comprising a detector plate mounted to the rotatable disc, the detector plate being configured to assume (i) a retracted position in which the detector plate is not aligned with the X-ray beam, whereby to permit the X-ray beam to contact the X-ray detector, and (ii) an extended position in which the detector plate is aligned with the X-ray beam, whereby to permit the X-ray beam to contact the detector plate.

In another preferred form of the invention, there is provided an imaging system for imaging an object, said imaging system comprising:
 a housing having a center opening;
 a CT imaging unit mounted to the housing, the CT imaging unit comprising:
  a rotatable disc extending around the center opening;
  an X-ray emitter mounted to the rotatable disc and configured to emit an X-ray beam; and
  an X-ray detector mounted to the rotatable disc in alignment with the X-ray beam; and
 an ultrasound imager.

In another preferred form of the invention, there is provided a method for imaging an object, the method comprising:
 providing an imaging system comprising:
  a housing having a center opening;
  a CT imaging unit mounted to the housing, the CT imaging unit comprising:
   a rotatable disc extending around the center opening;
   an X-ray emitter mounted to the rotatable disc and configured to emit an X-ray beam; and
   an X-ray detector mounted to the rotatable disc in alignment with the X-ray beam; and
  a digital radiography imager comprising a detector plate mounted to the rotatable disc, the detector plate being configured to assume (i) a retracted position in which the detector plate is not aligned with the X-ray beam, whereby to permit the X-ray beam to contact the X-ray detector, and (ii) an extended position in which the detector plate is aligned with the X-ray beam, whereby to permit the X-ray beam to contact the detector plate;
 positioning an object in the central opening;
 passing the X-ray beam through the object disposed in the central opening; and
 using one of the X-ray detector and the detector plate to detect the X-ray beam after it passes through the object disposed in the central opening.

In another preferred form of the invention, there is provided a method for imaging an object, the method comprising:
 providing an imaging system comprising:
  a housing having a center opening;
  a CT imaging unit mounted to the housing, the CT imaging unit comprising:
   a rotatable disc extending around the center opening;
   an X-ray emitter mounted to the rotatable disc and configured to emit an X-ray beam; and
   an X-ray detector mounted to the rotatable disc in alignment with the X-ray beam; and
  an ultrasound imager;
 positioning an object in the central opening; and
 using at least one of the CT imaging unit and the ultrasound imager to image the object in the central opening.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE PREFERRED EMBODIMENTS

Figure 1:
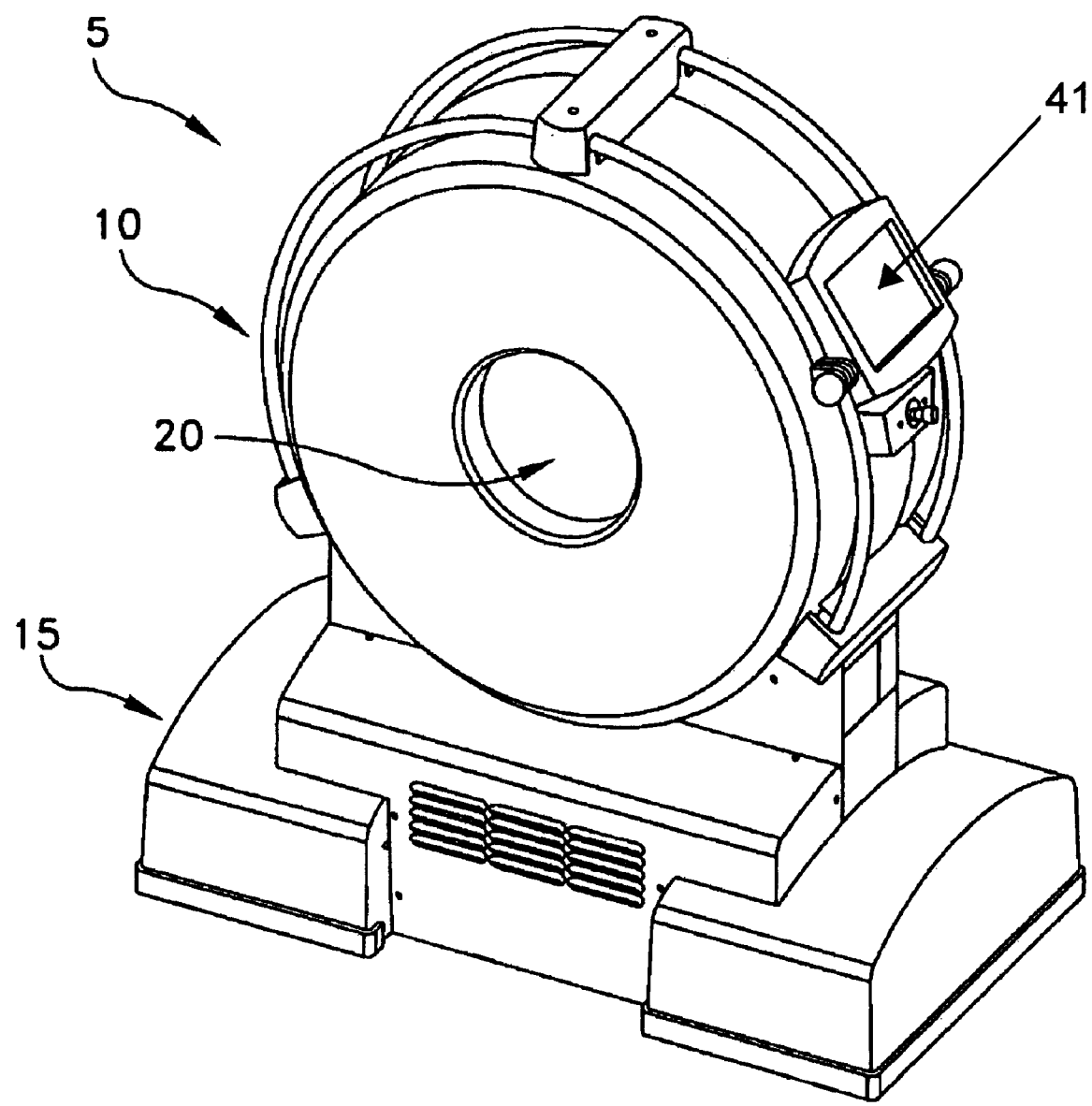
FIGS. 1 and 2 are schematic views showing the exterior of an exemplary CT imaging machine.
Figure 2:
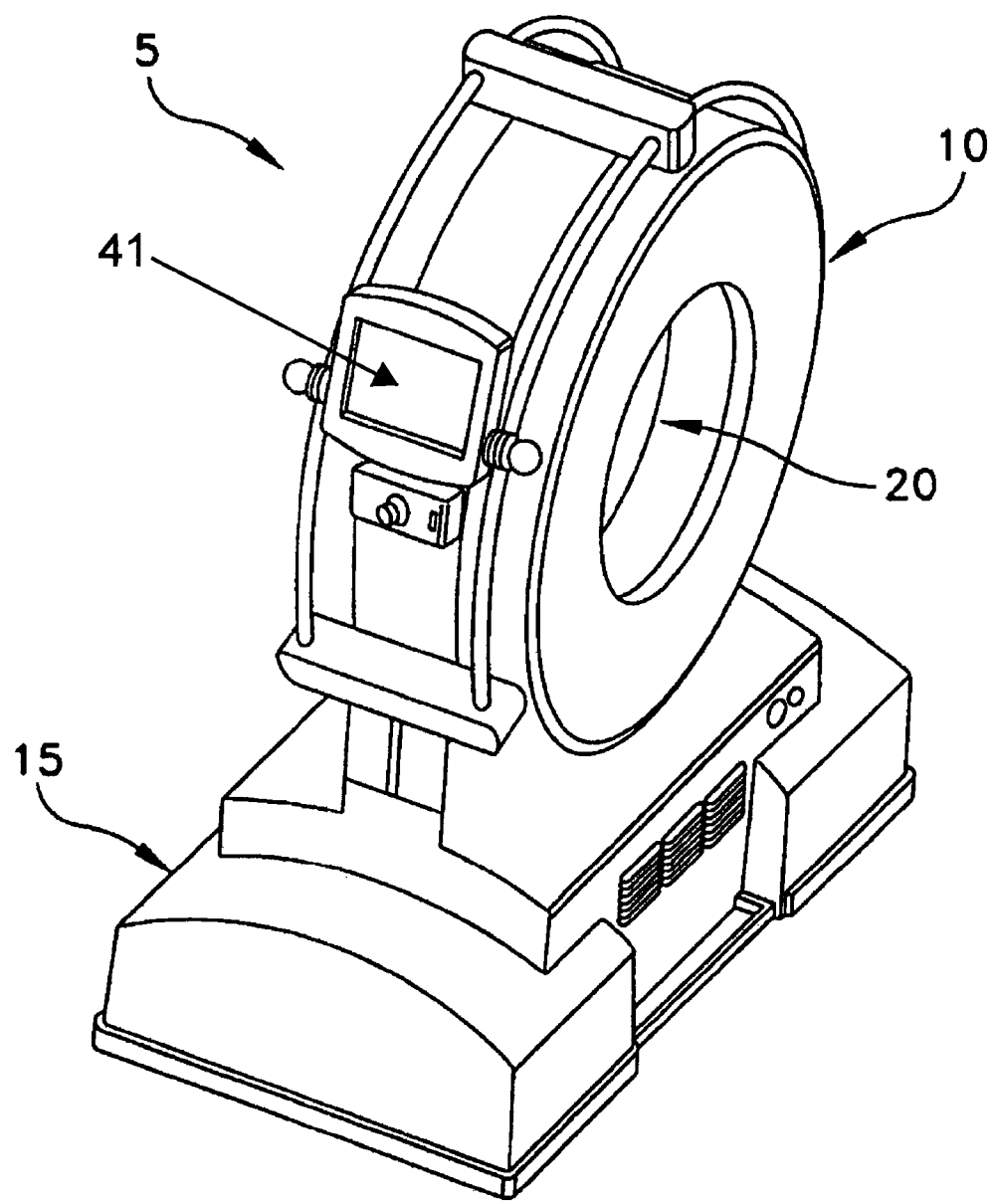
Figure 3:
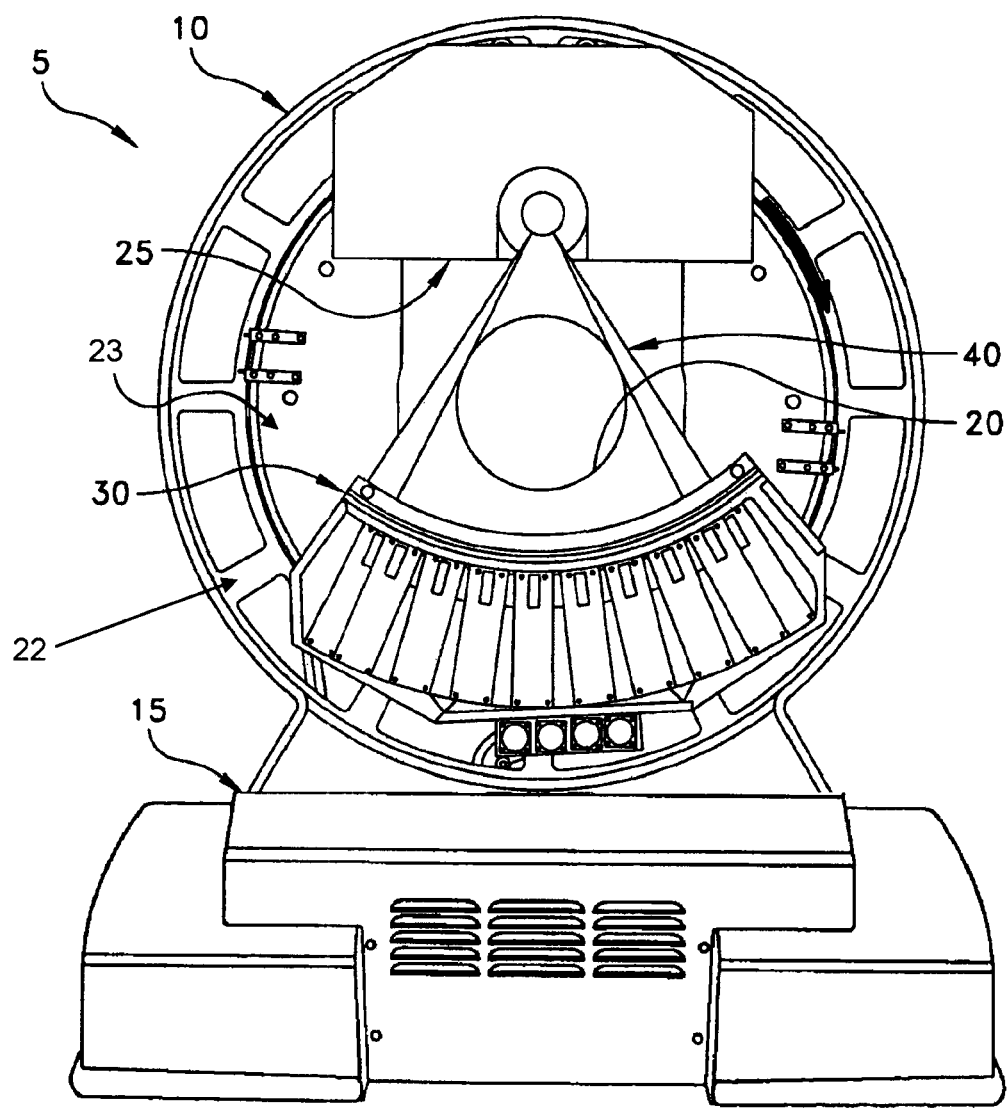
FIG. 3 is a schematic view showing various components in the torus of the exemplary CT imaging machine shown in FIGS. 1 and 2.
Figure 4:
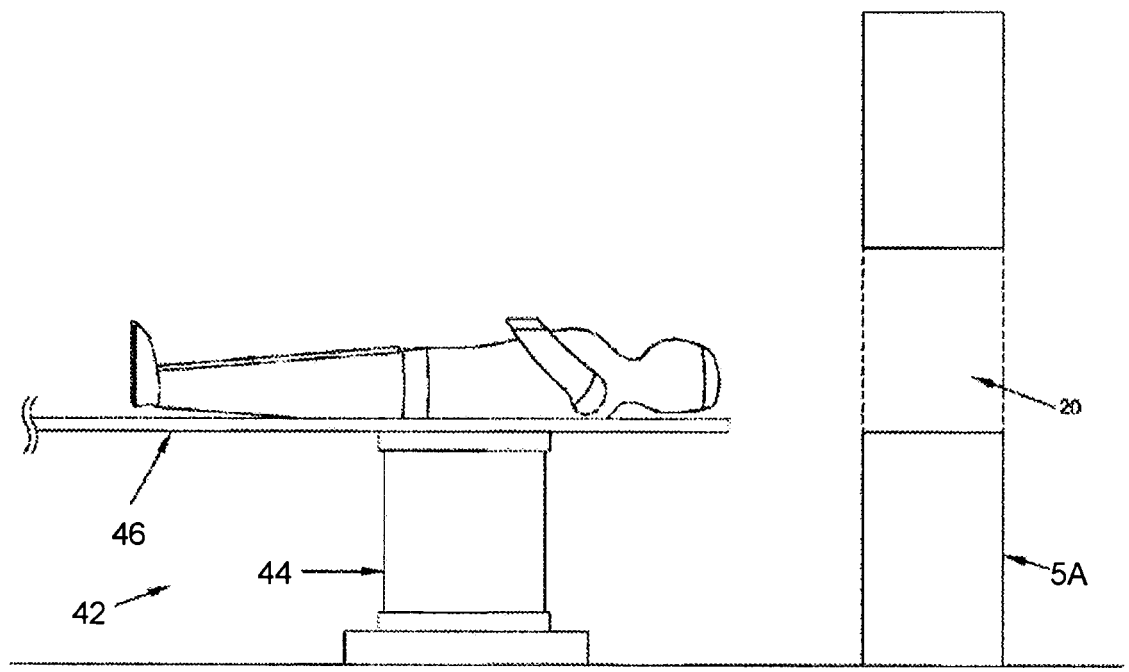
FIG. 4 is a schematic view showing an exemplary fixed CT imaging machine and a motorized bed.
Figure 5:
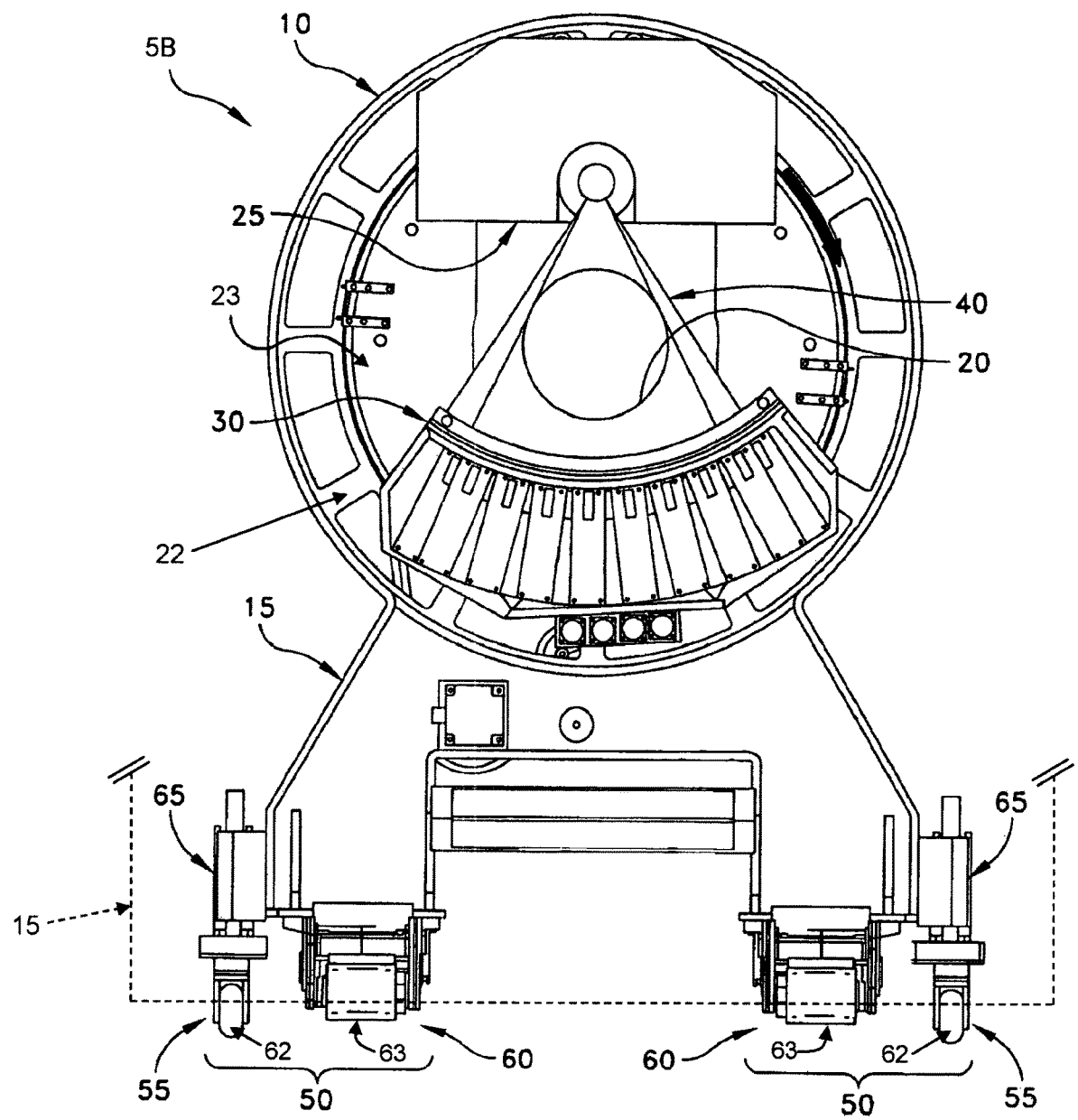
FIGS. 5 and 6 are schematic views showing an exemplary transport assembly for an exemplary mobile CT imaging machine.
Figure 6:
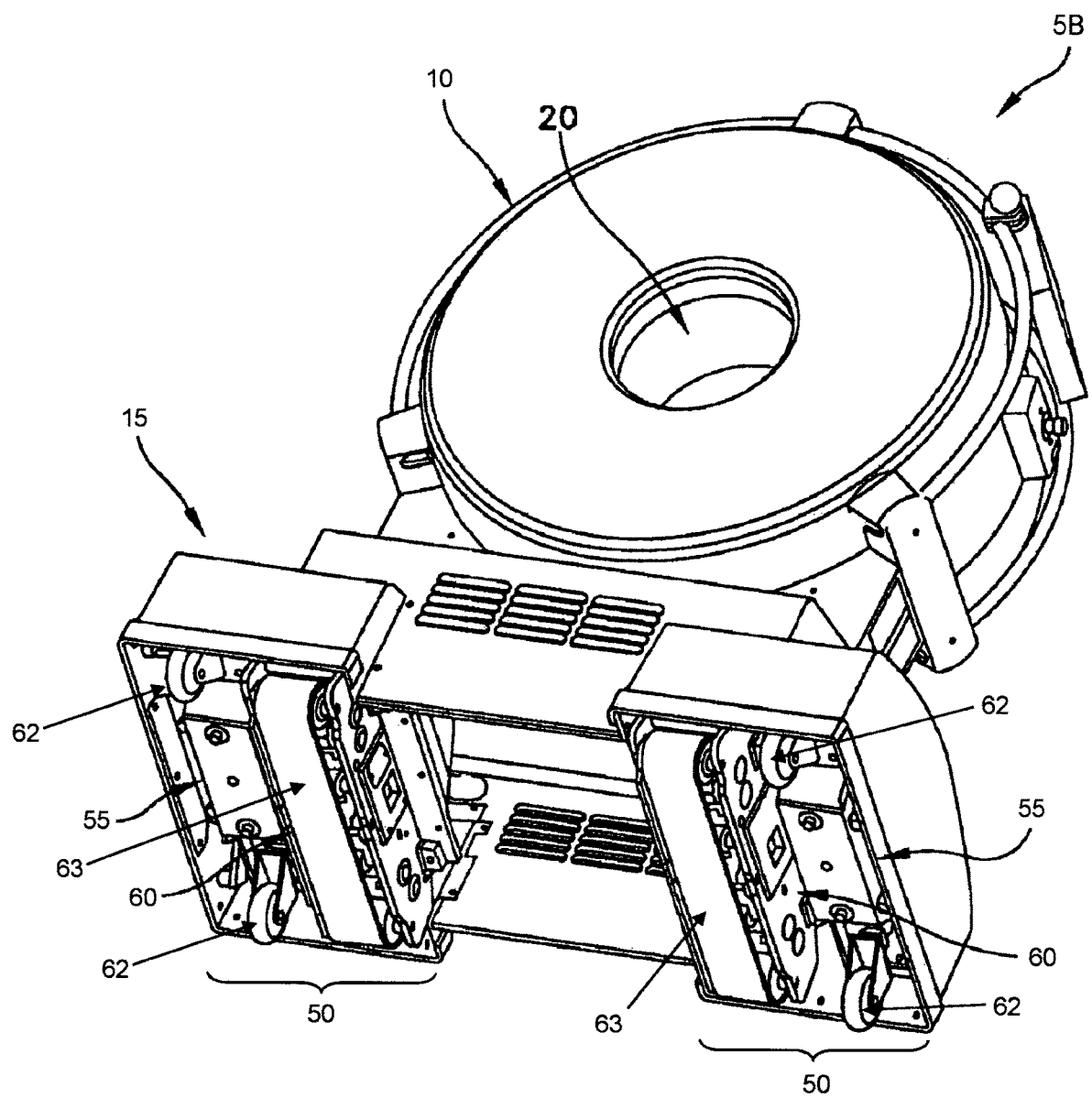
Figure 7:
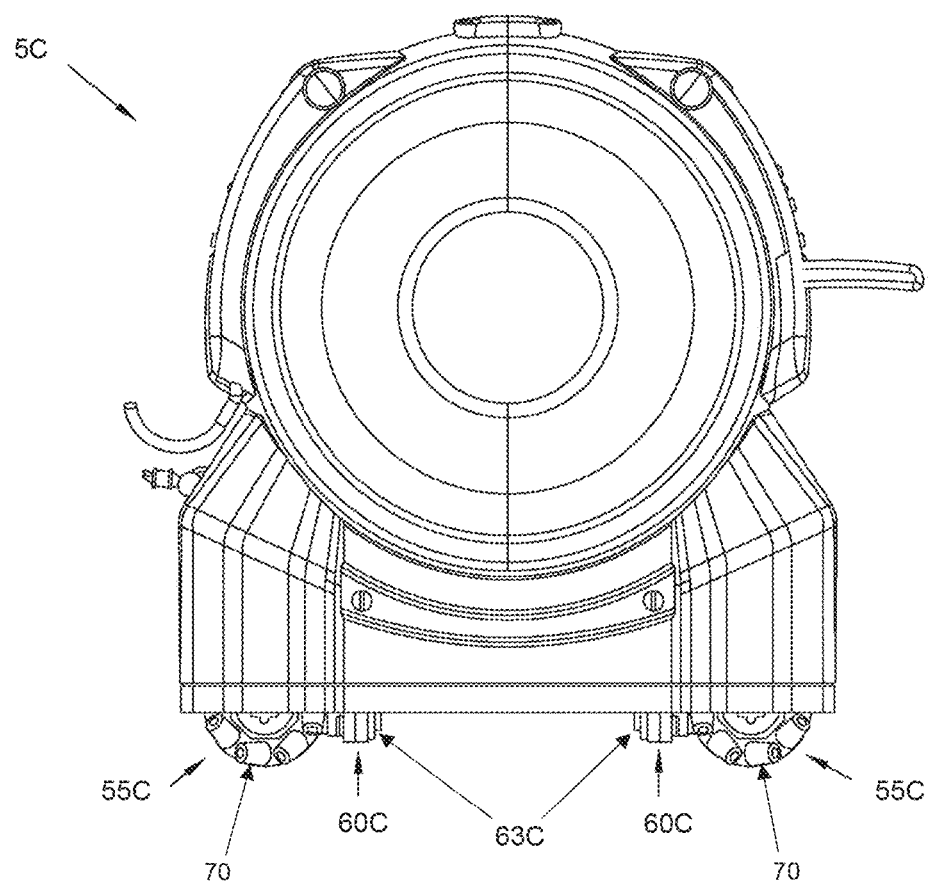
FIG. 7 is a schematic view showing another exemplary transport assembly for an exemplary mobile CT imaging machine.
Figure 8:
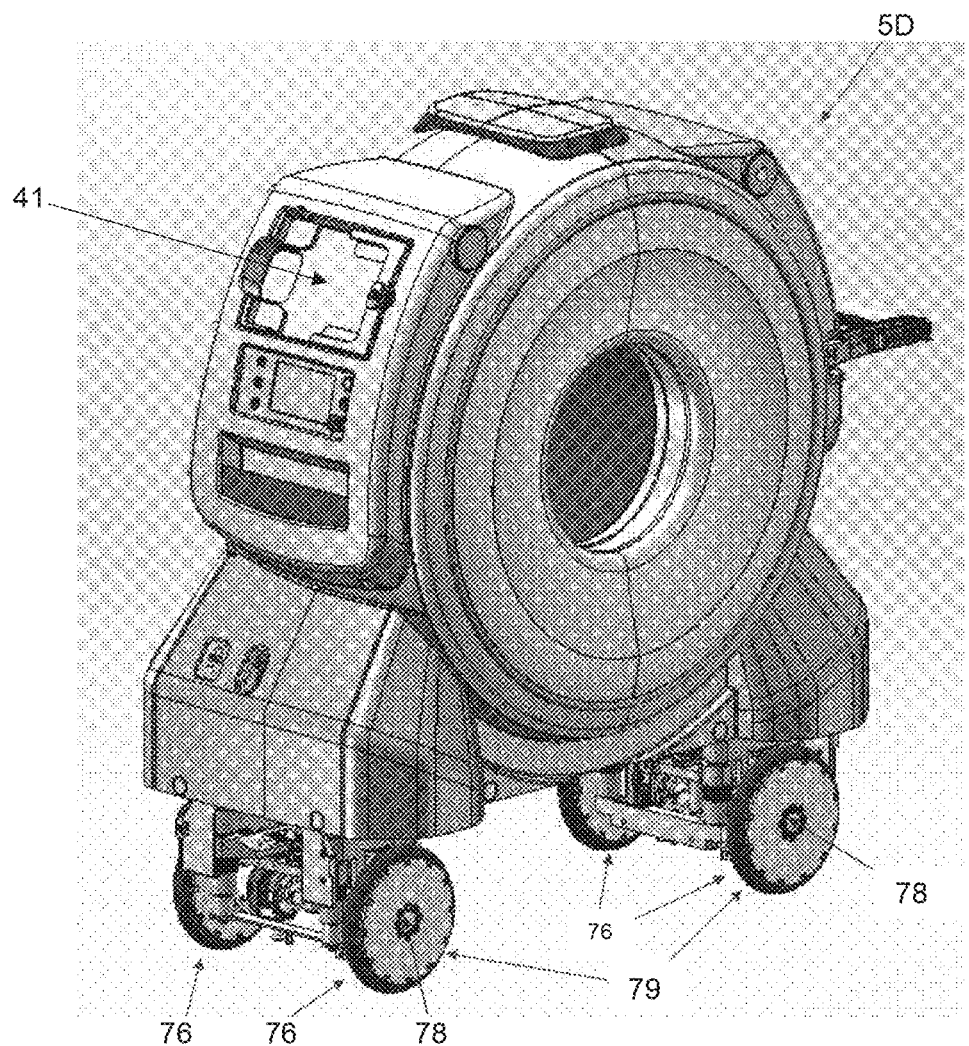
FIG. 8 is a schematic view showing still another exemplary transport assembly for an exemplary mobile CT imaging machine.
Figure 9:
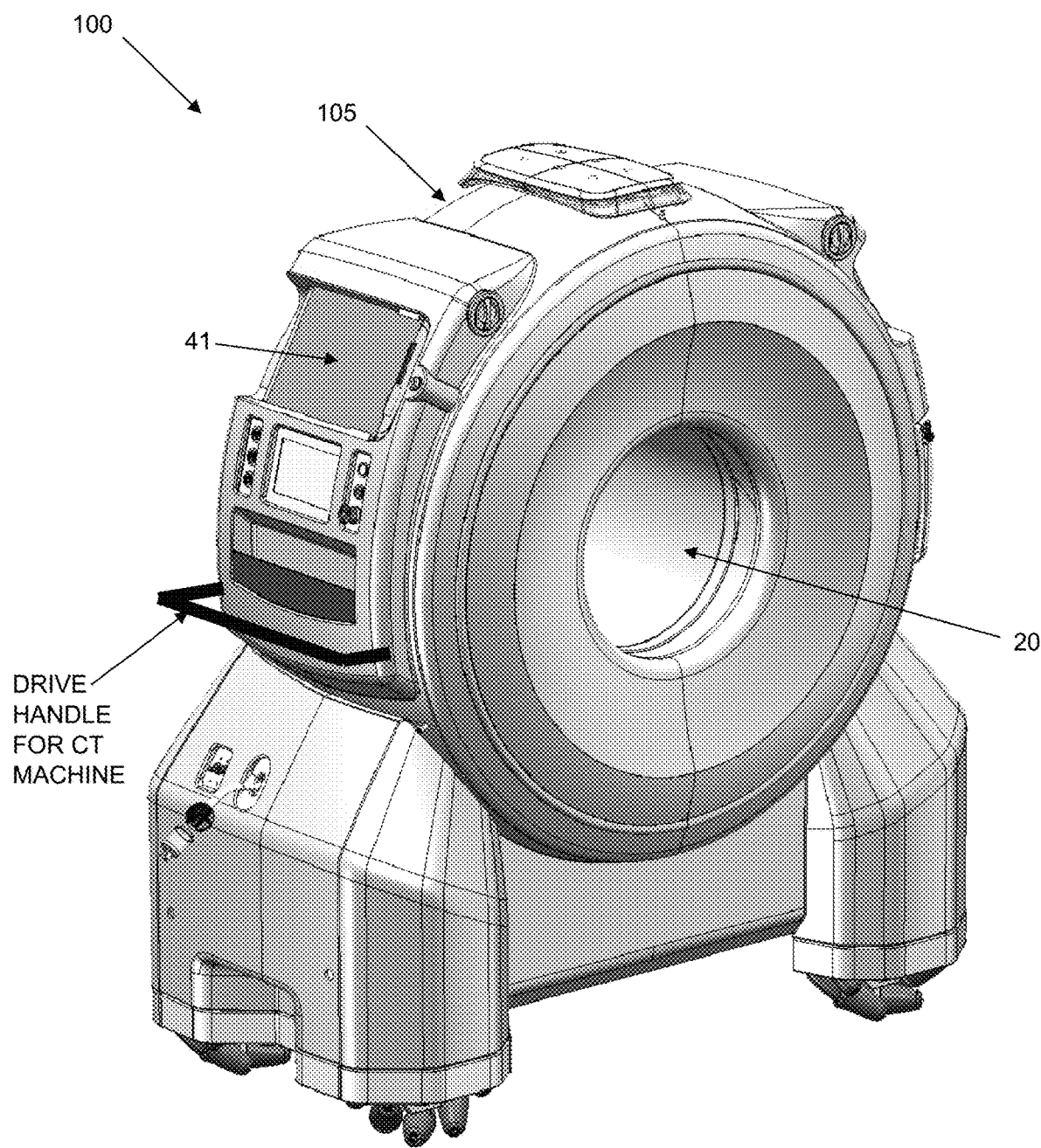
FIGS. 9-13 are schematic views showing a novel mobile CT imaging system formed in accordance with the present invention, the mobile CT imaging system comprising a mobile CT imaging machine with an on-board digital radiography imager.
Figure 10:
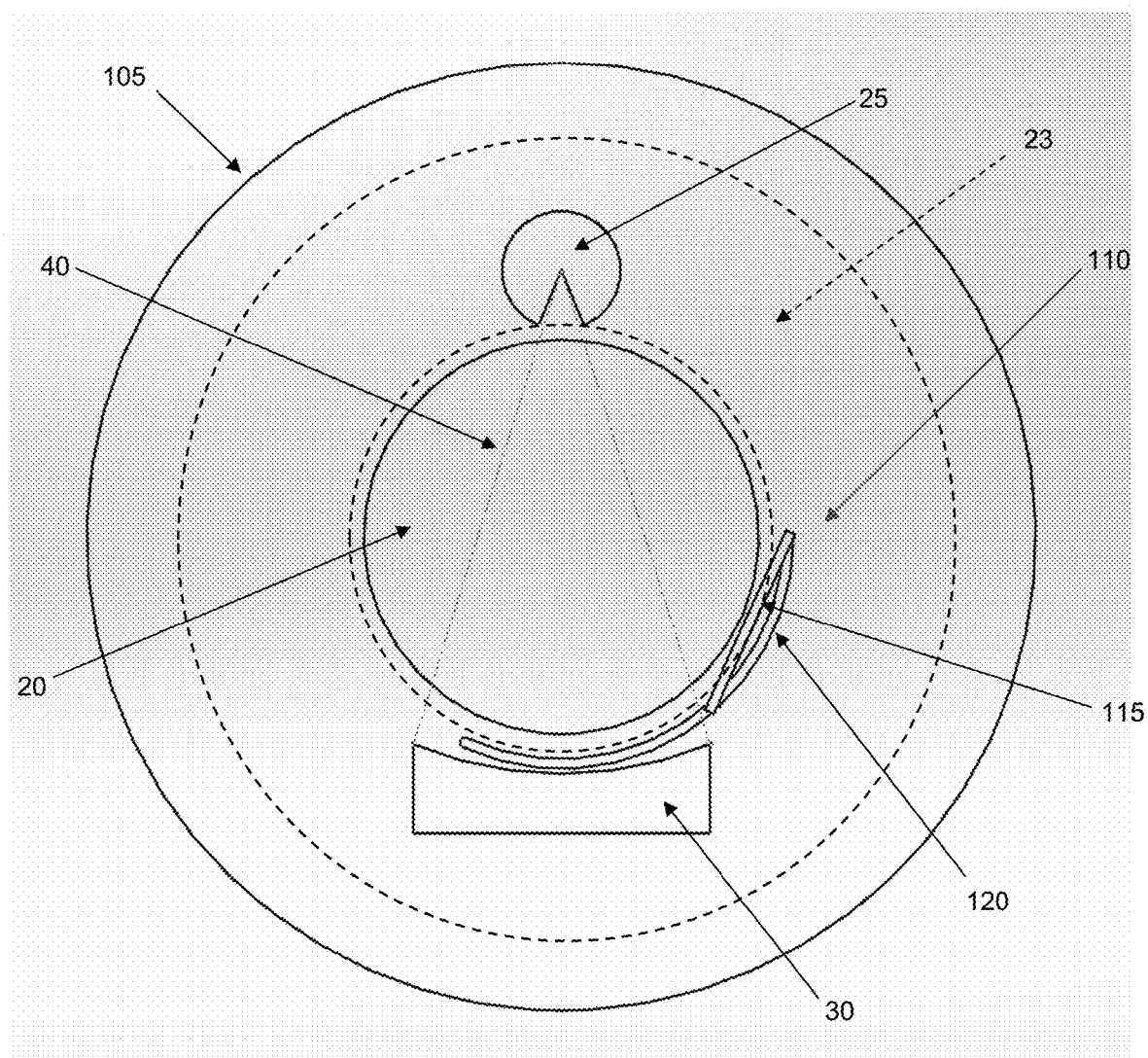
Figure 11:
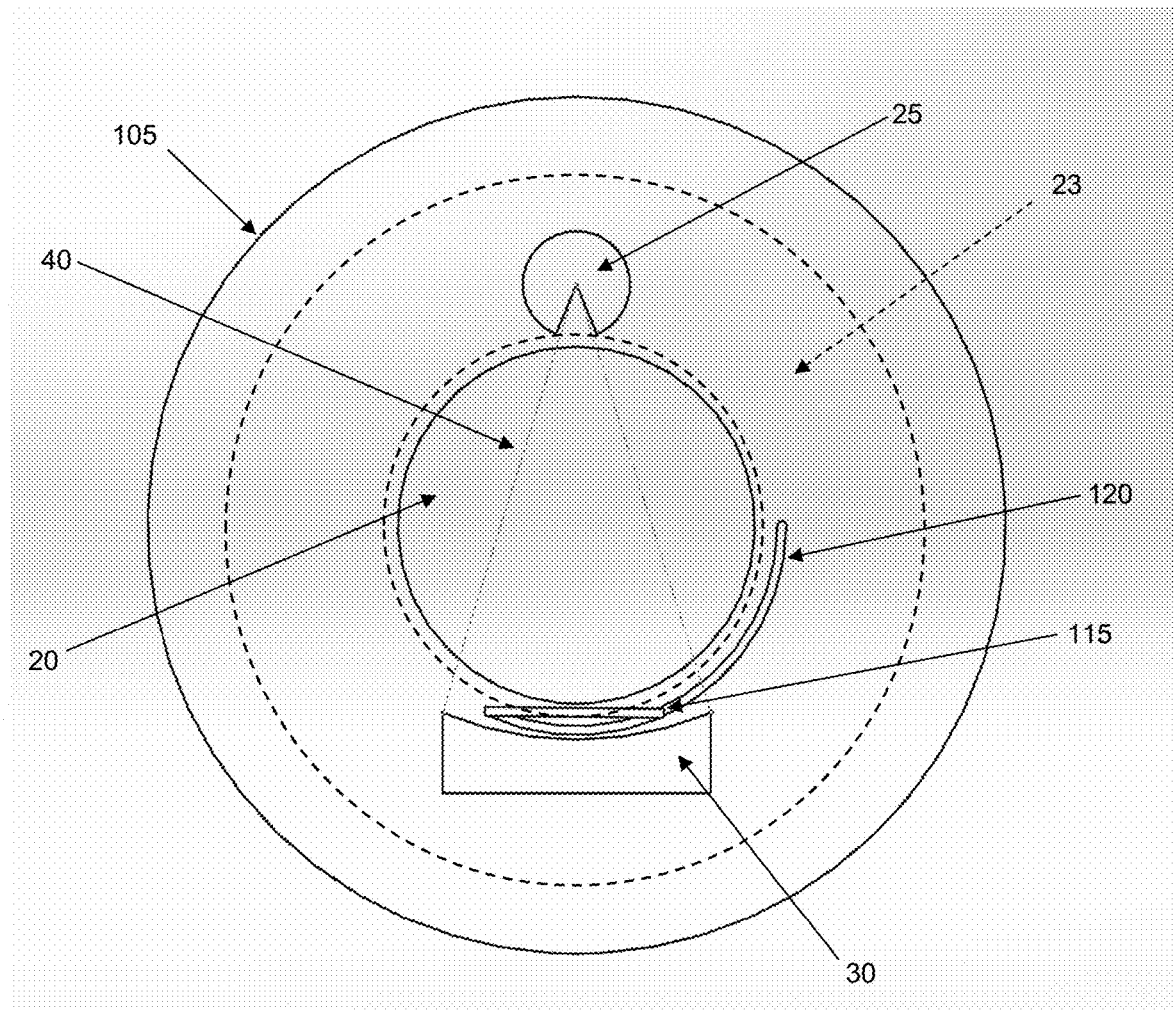
Figure 12:
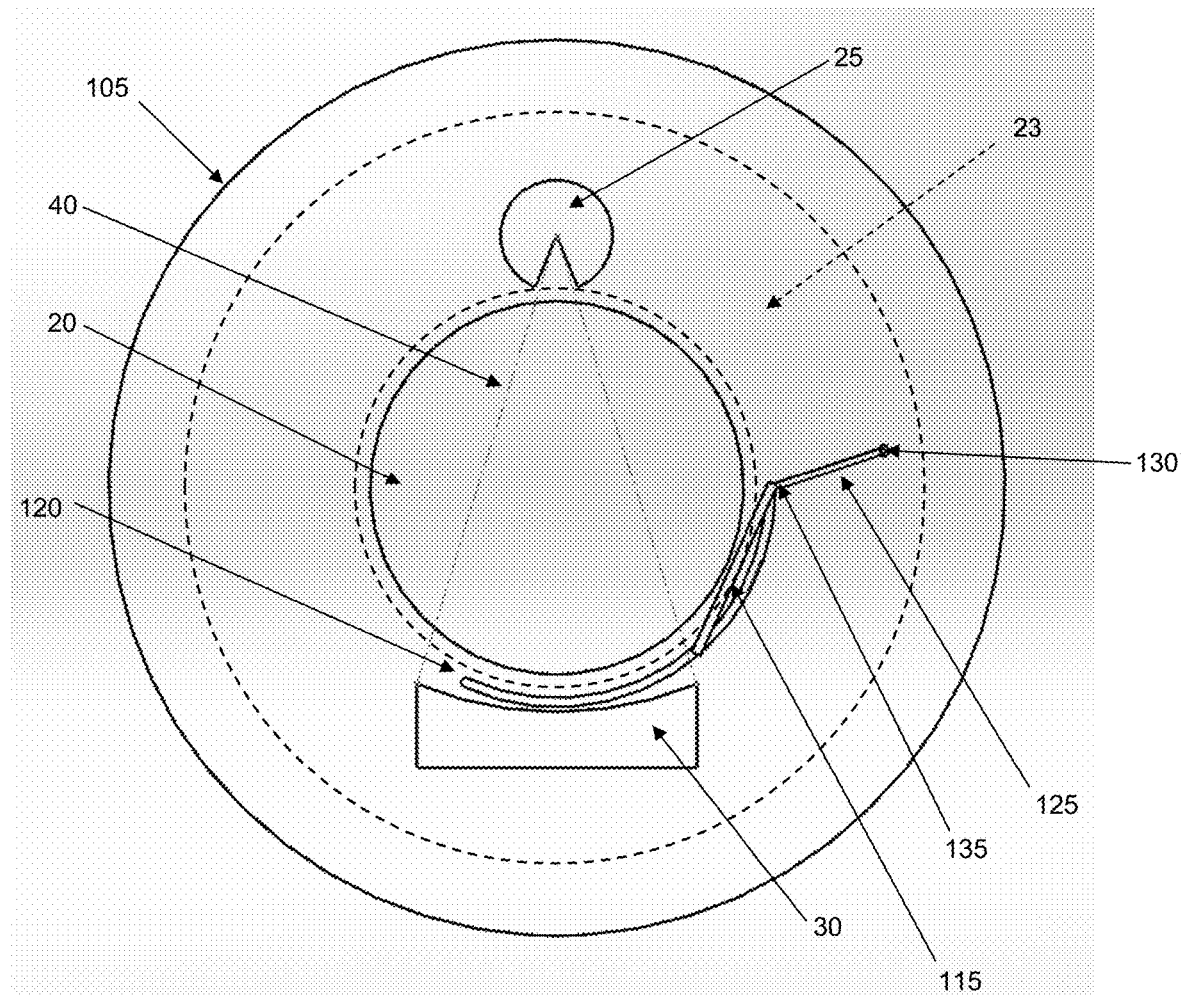
Figure 13:
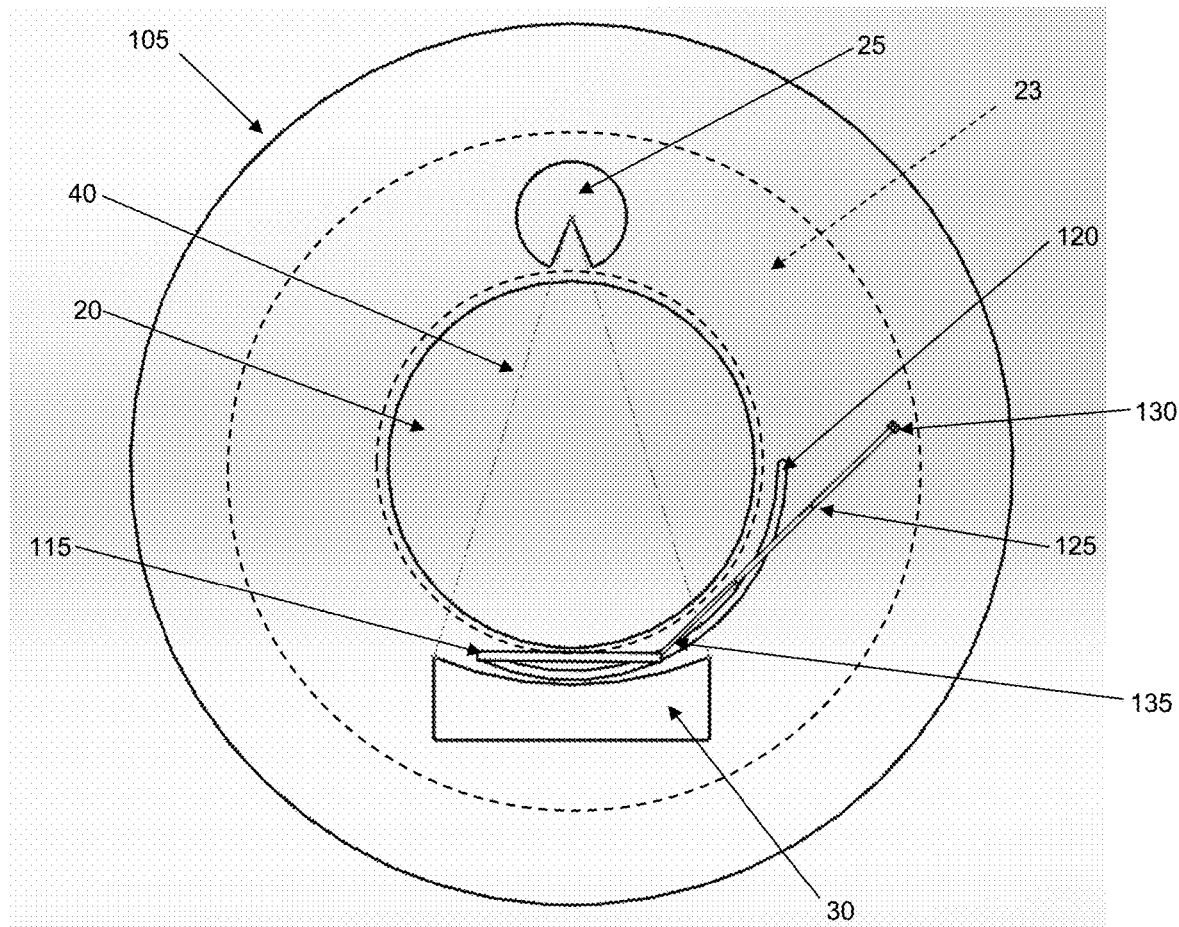

Novel Mobile CT Imaging System Comprising a Mobile CT Imaging Machine with an On-Board Digital Radiography Imager Looking first at FIGS. 9-13, there is shown a novel mobile CT imaging system 100 comprising a mobile CT imaging machine 105 with an on-board digital radiography imager 110.

Novel mobile CT imaging machine 105 may comprise the aforementioned mobile CT imaging machine 5B (i.e., where free-rolling castors 62 are used to move the system quickly between locations, and centipede belt drives 63 are used to move the machine during scanning); or novel mobile CT imaging machine 105 may comprise the aforementioned mobile CT imaging machine 5C (i.e., where powered mecanum wheels 70 (also known as "omni" wheels or "ilon" wheels) are used to move the machine quickly between locations, and powered wheels 63C are used to move the machine during scanning); or novel mobile CT imaging machine 105 may comprise the aforementioned mobile CT imaging machine 5D (i.e., where so-called "Liddiard" wheels 76 are used to move the machine both quickly between locations and during scanning); or novel mobile CT imaging machine 105 may comprise any other mobile CT imaging machine capable of moving between locations before and/or after scanning.

On-board digital radiography imager 110 is movably mounted to mobile CT imaging machine 105 such that on-board digital radiography imager 110 may be selectively interposed opposite to X-ray tube assembly 25, with the anatomy to be scanned interposed between the X-ray source (i.e., X-ray tube assembly 25) and on-board digital radiography imager 110 when it is desired to perform digital radiography imaging, and selectively moved out of position of the X-ray source (i.e., X-ray tube assembly 25) so as to expose X-ray detector assembly 30 to the X-ray source when it is desired to perform CT imaging, as will hereinafter be discussed in further detail.

More particularly, on-board digital radiography imager 110 generally comprises a detector plate 115 for selectively detecting X-rays emitted from X-ray tube assembly 25 which have passed through the anatomy disposed in center opening 20 of mobile CT imaging machine 105 when detector plate 115 is positioned opposite X-ray tube assembly 25 with the anatomy to be scanned disposed between detector plate 115 and X-ray tube assembly 25. To this end, on-board digital radiography imager 110 is configured to be capable of selectively assuming: (i) a first "retracted" position (which also may be referred to herein as a "standby" position) (see FIGS. 10 and 12) in which detector plate 115 is not diametrically-opposed to X-ray tube assembly 25 and is not positioned in front of X-ray detector assembly 30, whereby to enable CT imaging via X-ray tube assembly 25 and X-ray detector assembly 30, and (ii) a second "extended" position (which also may be referred to herein as a "scanning" position) (see FIGS. 11 and 13) in which detector plate 115 is diametrically-opposed to X-ray tube assembly 25 and is positioned in front of X-ray detector assembly 30 such that the anatomy to be scanned can be interposed between X-ray tube assembly 25 and detector plate 115 (i.e., by disposing the anatomy which is to be scanned inside center opening 20), whereby to enable digital radiography imaging of the anatomy disposed in center opening 20 via X-ray tube assembly 25 and detector plate 115.

To this end, on-board digital radiography imager 110 comprises powered systems configured to selectively move detector plate 115 between its first "retracted" position and its second "extended" position.

More particularly, in one preferred form of the present invention, on-board digital radiography imager 110 comprises at least one rail 120 mounted to rotating disc 23, with detector plate 115 being slidably mounted to the at least one rail 120 so that detector plate 115 can be selectively moved between its first "retracted" position and its second "extended" position. In a preferred form of the present invention, and looking now at FIG. 12, detector plate 115 is preferably moved on the at least one rail 120 by means of one or more telescoping arms 125. The one or more telescoping arms 125 generally comprise a first end 130 pivotally mounted to rotating disc 23, and a second end 135 which is pivotally mounted to detector plate 115. In this way, retracting the one or more telescoping arms 125 causes detector plate 115 to assume its first "retracted" position, and extending the one or more telescoping arms 125 causes detector plate 115 to assume its second "extended" position.

In use, when mobile CT imaging system 100 is to be used for CT imaging, detector plate 115 is placed into its first "retracted" position (i.e., where detector plate 115 is not diametrically-opposed to X-ray tube assembly 25 and is not positioned in front of X-ray detector assembly 30), and then mobile CT imaging machine 105 is used in the traditional manner to produce CT images of anatomy disposed in the central opening 20 (i.e., with rotating disc 23 moving, X-ray tube assembly 25 emits X-ray beam 40 and X-ray detector assembly 30 detects the X-ray beam 40 passing through the anatomy along a full range of radial positions, so as to enable CT imaging). When mobile CT imaging system 100 is to be used for digital radiography, detector plate 115 is moved into its second "extended" position (i.e., by extending the one or more telescoping arms 125 in order to dispose detector plate 115 diametrically-opposed to X-ray tube assembly 25 with detector plate 115 positioned in front of X-ray detector assembly 30), and then mobile CT imaging machine 105 is used to produce digital radiography images of anatomy disposed in central opening 20 (i.e., with rotating disc 23 stationary, X-ray tube assembly 25 emits X-ray beam 40 and detector plate 115 detects the X-ray beam 40 passing through the anatomy at a single position, so as to enable digital radiography imaging). Note that when mobile CT imaging system 100 is to be used for digital radiography, the rotational position of rotating disc 23 may be adjusted as needed to provide the desired angle of imaging.

Thus, with the present invention, the same X-ray tube assembly 25 may be used for CT imaging as well as for digital radiography imaging. It should be appreciated that the power level of X-ray beam 40 (and hence the amount of radiation) emitted by X-ray tube assembly 25 can be adjusted depending on whether the X-ray tube assembly 25 is being used for CT imaging or for digital radiography imaging. By way of example but not limitation, the power level of X-ray beam 40 may be significantly reduced when it is desired to use novel mobile CT imaging system 100 to perform digital radiography imaging. Thus, with the present invention, it is possible to reduce the amount of radiation exposure to the patient when higher energy X-rays are not required to perform the desired imaging (e.g., when performing digital radiography imaging).

Novel Mobile CT Imaging System Comprising an On-Board Ultrasound Imager

Figure 14:
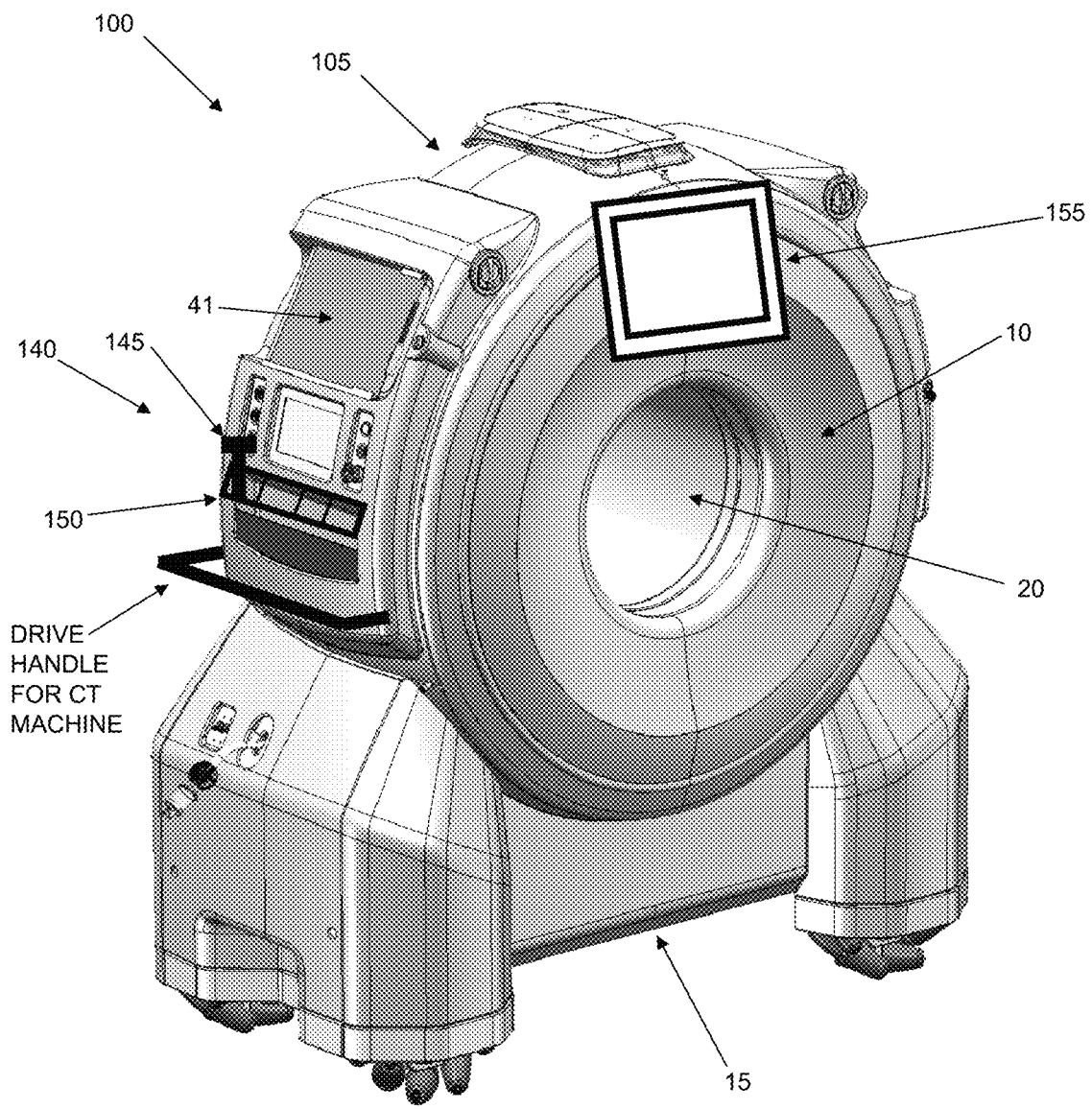
FIG. 14 is a schematic view showing a novel mobile CT imaging system formed in accordance with the present invention, the mobile CT imaging system comprising a mobile CT imaging machine with an on-board ultrasound imager.

Looking next at FIG. 14, in another form of the invention, novel mobile CT imaging system 100 may comprise a mobile CT imaging machine 105 with an on-board ultrasound imager 140 (either in addition to on-board digital radiography imager 110 or without on-board digital radiography imager 110). More particularly, on-board ultrasound imager 140 generally comprises an ultrasound wand 145 which can be stored on a rack 150 on mobile CT imaging machine 105, and an adjustable viewing screen 155 for displaying the images obtained by ultrasound wand 145.

More particularly, ultrasound wand 145 comprises an emitter configured to emit sound waves having a frequency appropriate for imaging, and a probe configured to detect reflected sound waves, as will be apparent to one of ordinary skill in the art. Ultrasound wand 145 may be wireless, or ultrasound wand 145 may be connected to CT imaging machine 105 via one or more wires. The supporting electronics for on-board ultrasound imager 140 may be housed in the torus 10 and/or base 15 of mobile CT imaging machine 105.

Thus, with the present invention, the same mobile CT imaging system 100 may be used to perform CT imaging, digital radiography imaging and ultrasound imaging.

Application to Other Types of Scanning Systems

It should be appreciated that the present invention is not limited to use in medical applications or, indeed, to use with CT machines. Thus, for example, the present invention may be used in connection with mobile CT machines used for non-medical applications, e.g., with mobile CT machines used to scan inanimate objects. Furthermore, the present invention may be used with non-CT-type mobile scanning systems. Thus, for example, the present invention may be used in conjunction with mobile SPECT machines, mobile MRI machines, mobile PET machines, mobile X-ray machines, etc., i.e., wherever the mobile scanning machine may require close tracking to a scan path.

Modifications

It will be appreciated that still further embodiments of the present invention will be apparent to those skilled in the art in view of the present disclosure. It is to be understood that the present invention is by no means limited to the particular constructions herein disclosed and/or shown in the drawings, but also comprises any modifications or equivalents within the scope of the invention.

What is claimed is:

1. An imaging system for imaging an object, the imaging system comprising:
a housing having a center opening;
a CT imaging unit mounted to the housing, the CT imaging unit comprising:
a rotatable disc extending around the center opening;
an X-ray emitter mounted to the rotatable disc and configured to emit an X-ray beam; and
an X-ray detector mounted to the rotatable disc in alignment with the X-ray beam; and
a digital radiography imager comprising a detector plate mounted to the rotatable disc, the detector plate being configured to assume (i) a retracted position in which the detector plate is not aligned with the X-ray beam, whereby to permit the X-ray beam to contact the X-ray detector, and (ii) an extended position in which the detector plate is aligned with the X-ray beam, whereby to permit the X-ray beam to contact the detector plate.

2. The imaging system according to claim 1 wherein the X-ray emitter is configured to emit an X-ray beam having a first power level when the detector plate is disposed in its retracted position, and wherein the X-ray emitter is configured to emit an X-ray beam having a second power level when the detector plate is disposed in its extended position.

3. The imaging system according to claim 2 wherein the first power level is greater than the second power level.

4. The imaging system according to claim 1, further comprising a motor for moving the detector plate between its retracted position and its extended position.

5. The imaging system according to claim 1 wherein the detector plate is slidably mounted to the rotatable disc.

6. The imaging system according to claim 5 wherein the CT imaging unit comprises a rail and at least one telescoping arm for slidably moving the detector plate along the rail.

7. The imaging system according to claim 1 further comprising an ultrasound imager.

8. The imaging system according to claim 1 wherein the housing comprises a transport mechanism for moving the CT imaging unit, wherein the transport mechanism comprises (i) a gross movement mechanism for transporting the CT imaging unit across room distances, and (ii) a fine movement mechanism for moving the CT imaging unit precisely, relative to a patient, during scanning.

9. An imaging system for imaging an object, said imaging system comprising:
a housing having a center opening;
a CT imaging unit mounted to the housing, the CT imaging unit comprising:
a rotatable disc extending around the center opening;
an X-ray emitter mounted to the rotatable disc and configured to emit an X-ray beam; and
an X-ray detector mounted to the rotatable disc in alignment with the X-ray beam; and
an ultrasound imager.

10. The imaging system according to claim 9 wherein the housing comprises a cradle for receiving the ultrasound imager.

11. The imaging system according to claim 9 further comprising a visual display for displaying data obtained by the ultrasound imager.

12. The imaging system according to claim 1 wherein the housing comprises a transport mechanism for moving the CT imaging unit, wherein the transport mechanism comprises (i) a gross movement mechanism for transporting the CT imaging unit across room distances, and (ii) a fine movement mechanism for moving the CT imaging unit precisely, relative to a patient, during scanning.

13. A method for imaging an object, the method comprising:
providing an imaging system comprising:
a housing having a center opening;
a CT imaging unit mounted to the housing, the CT imaging unit comprising:
a rotatable disc extending around the center opening;
an X-ray emitter mounted to the rotatable disc and configured to emit an X-ray beam; and
an X-ray detector mounted to the rotatable disc in alignment with the X-ray beam; and
a digital radiography imager comprising a detector plate mounted to the rotatable disc, the detector plate being configured to assume (i) a retracted position in which the detector plate is not aligned with the X-ray beam, whereby to permit the X-ray beam to contact the X-ray detector, and (ii) an extended position in which the detector plate is aligned with the X-ray beam, whereby to permit the X-ray beam to contact the detector plate;
positioning an object in the center opening;
passing the X-ray beam through the object disposed in the center opening; and
using one of the X-ray detector and the detector plate to detect the X-ray beam after it passes through the object disposed in the center opening.

14. The method according to claim 13 wherein using one of the X-ray detector and the detector plate to detect the X-ray beam comprises moving the detector plate to its extended position so that the detector plate detects the X-ray beam.

15. A method for imaging an object, the method comprising:
  providing an imaging system comprising:
    a housing having a center opening;
    a CT imaging unit mounted to the housing, the CT imaging unit comprising:
      a rotatable disc extending around the center opening;
      an X-ray emitter mounted to the rotatable disc and configured to emit an X-ray beam; and
      an X-ray detector mounted to the rotatable disc in alignment with the X-ray beam; and
    an ultrasound imager;
  positioning an object in the center opening; and
  using at least one of the CT imaging unit and the ultrasound imager to image the object in the center opening.

* * * * *